(12) United States Patent
Zareie et al.

(10) Patent No.: US 8,527,211 B2
(45) Date of Patent: Sep. 3, 2013

(54) METHOD TO PRODUCE RECOMBINANT MBP8298 AND OTHER POLYPEPTIDES BY NUCLEOTIDE STRUCTURE OPTIMIZATION

(76) Inventors: Reza Zareie, Isfahan (IR); Mahdi Abbasian, Isfahan (IR)

( * ) Notice: Subject to any disclaimer, the term of this patent is extended or adjusted under 35 U.S.C. 154(b) by 235 days.

(21) Appl. No.: 12/457,658

(22) Filed: Jun. 17, 2009

(65) Prior Publication Data
US 2011/0008827 A1    Jan. 13, 2011

Related U.S. Application Data

(60) Provisional application No. 61/073,369, filed on Jun. 18, 2008.

(51) Int. Cl.
*G01N 31/00*    (2006.01)

(52) U.S. Cl.
USPC .......................................................... 702/27

(58) Field of Classification Search
USPC .......................................................... 702/27
See application file for complete search history.

*Primary Examiner* — Jerry Lin
(74) *Attorney, Agent, or Firm* — Barry Choobin; Choobin & Choobin Consultancy L.L.C.

(57) ABSTRACT

A method for recombinant production of a polypeptide, exemplified by the therapeutic peptide MBP8298, by recombining and optimizing the nucleic acid encoding said polypeptide, expressing said nucleic acid in a microbial host cell, isolating said polypeptide from the host, and releasing embedded polypeptide from fusion partners or peptide concatamers are explained. Such method may provide increased production or simplified downstream processing for the polypeptide of interest.

7 Claims, 8 Drawing Sheets

SEQUENCE LISTING

```
<160> NUMBER OF SEQ ID NOS: 18

<210> SEQ ID NO 1
<211> LENGTH: 17
<212> TYPE: PRT
<213> ORGANISM: Homo sapiens

<400> SEQUENCE: 1

Asp Glu Asn Pro Val Val His Phe Phe Lys Asn Ile Val Thr Pro Arg
1               5                   10                  15

Thr

<210> SEQ ID NO 2
<211> LENGTH: 29
<212> TYPE: DNA
<213> ORGANISM: Artificial Sequence
<220> FEATURE:
<223> OTHER INFORMATION: Left primer for Medicago truncatula ubiquitin
      gene

<400> SEQUENCE: 2
tatacatatg caaatcttcg ttaagaccc                                         29

<210> SEQ ID NO 3
<211> LENGTH: 22
<212> TYPE: DNA
<213> ORGANISM: Artificial Sequence
```

```
<220> FEATURE:
<223> OTHER INFORMATION: Right primer for Medicago truncatula ubiquitin
      gene

<400> SEQUENCE: 3
attagctagc accaccacgg ag                                                  22

<210> SEQ ID NO 4
<211> LENGTH: 237
<212> TYPE: DNA
<213> ORGANISM: Medicago truncatula
<220> FEATURE:
<221> NAME/KEY: misc_feature
<222> LOCATION: (1)..(237)
<223> OTHER INFORMATION: PCR product
<220> FEATURE:
<221> NAME/KEY: CDS
<222> LOCATION: (4)..(231)
<223> OTHER INFORMATION: Medicago truncatula ubiquitin

<400> SEQUENCE: 4 cat atg caa atc ttc gtt aag acc ctc act gga aag acc atc act ctc        48
    Met Gln Ile Phe Val Lys Thr Leu Thr Gly Lys Thr Ile Thr Leu
    1               5                  10                  15 gaa gtt gag agt tca gat acc ata gac aat gtt aag gca aag att caa        96
Glu Val Glu Ser Ser Asp Thr Ile Asp Asn Val Lys Ala Lys Ile Gln
                20                  25                  30 gac aag gaa gga atc cca cct gac cag cag cgt ctg att ttt gct gga       144
Asp Lys Glu Gly Ile Pro Pro Asp Gln Gln Arg Leu Ile Phe Ala Gly
            35                  40                  45 aag cag ctg gag gat ggg cgt acc ctt gct gat tat aac atc cag aag       192
Lys Gln Leu Glu Asp Gly Arg Thr Leu Ala Asp Tyr Asn Ile Gln Lys
        50                  55                  60 gag tcc acc ctc cat ttg gtg ctc cgt ctc cgt ggt ggt gctagc            237
Glu Ser Thr Leu His Leu Val Leu Arg Leu Arg Gly Gly
        65                  70                  75

<210> SEQ ID NO 5
<211> LENGTH: 76
<212> TYPE: PRT
<213> ORGANISM: Medicago truncatula

<400> SEQUENCE: 5

Met Gln Ile Phe Val Lys Thr Leu Thr Gly Lys Thr Ile Thr Leu Glu
1               5                  10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly
65                  70                  75

<210> SEQ ID NO 6
<211> LENGTH: 44
<212> TYPE: DNA
<213> ORGANISM: Artificial Sequence
<220> FEATURE:
<223> OTHER INFORMATION: Stem-loop inducing sequence, strand 1

<400> SEQUENCE: 6
tatgaaatat acatattctc tgcacgtgat cgtgcaggct agcg                        44
```

```
<210> SEQ ID NO 7
<211> LENGTH: 44
<212> TYPE: DNA
<213> ORGANISM: Artificial Sequence
<220> FEATURE:
<223> OTHER INFORMATION: Stem-loop inducing sequence, strand 2

<400> SEQUENCE: 7
ggcgctagcc tgcacgatca cgtgcagaga atatgtatat ttca          44

<210> SEQ ID NO 8
<211> LENGTH: 55
<212> TYPE: DNA
<213> ORGANISM: Artificial Sequence
<220> FEATURE:
<223> OTHER INFORMATION: MBP8298-encoding sequence, strand 1
<220> FEATURE:
<221> NAME/KEY: misc_feature
<222> LOCATION: (1)..(1)
<223> OTHER INFORMATION: Phosphorilated at the 5' site

<400> SEQUENCE: 8
ccgatgagaa tccggtggtg cacttcttca agaacatcgt gacgccacgc accga     55

<210> SEQ ID NO 9
<211> LENGTH: 51
<212> TYPE: DNA
<213> ORGANISM: Artificial Sequence
<220> FEATURE:
<223> OTHER INFORMATION: MBP8298-encoding sequence, strand 2
<220> FEATURE:
<221> NAME/KEY: misc_feature
<222> LOCATION: (1)..(1)
<223> OTHER INFORMATION: Phosphorilated at the 5' site.

<400> SEQUENCE: 9
ggtgcgtggc gtcacgatgt tcttgaagaa gtgcaccacc ggattctcat c          51

<210> SEQ ID NO 10
<211> LENGTH: 47
<212> TYPE: DNA
<213> ORGANISM: Artificial Sequence
<220> FEATURE:
<223> OTHER INFORMATION: MBP8298-encoding sequence, strand 3
<220> FEATURE:
<221> NAME/KEY: misc_feature
<222> LOCATION: (1)..(1)
<223> OTHER INFORMATION: Phosphorilated at the 5' site.

<400> SEQUENCE: 10
tgagaatccg gtggtgcact tcttcaagaa catcgtgacg ccacgca          47

<210> SEQ ID NO 11
<211> LENGTH: 25
<212> TYPE: DNA
<213> ORGANISM: Artificial Sequence
<220> FEATURE:
<223> OTHER INFORMATION: His-tag-encoding sequence, strand 1

<400> SEQUENCE: 11
ccgatcatca tcatcaccat cacta          25

<210> SEQ ID NO 12
<211> LENGTH: 27
<212> TYPE: DNA
<213> ORGANISM: Artificial Sequence
<220> FEATURE:
<223> OTHER INFORMATION: His-tag-encoding sequence, strand 2

<400> SEQUENCE: 12
```

-continued

```
agcttagtga tggtgatgat gatgatc                                         27
```

<210> SEQ ID NO 13
<211> LENGTH: 312
<212> TYPE: RNA
<213> ORGANISM: Artificial Sequence
<220> FEATURE:
<223> OTHER INFORMATION: Predicted mRNA sequence for M2H expressed in
      pET21c
<220> FEATURE:
<221> NAME/KEY: RBS
<222> LOCATION: (57)..(87)
<223> OTHER INFORMATION: RBS covers a region starting from approximately
      15 nucleotides before the AUG start codon and ending at
      approximately 13 nucleotides after it.
<220> FEATURE:
<221> NAME/KEY: CDS
<222> LOCATION: (72)..(209)

<400> SEQUENCE: 13

```
ggggaauugu gagcggauaa caauuccccu cuagaaauaa uuuuguuuaa cuuuaagaag      60
gagauauaca u aug gcu agc gcc gau gag aau ccg gug gug cac uuc uuc     110
             Met Ala Ser Ala Asp Glu Asn Pro Val Val His Phe Phe
             1               5                  10 aag aac auc gug acg cca cgc acc gau gag aau ccg gug gug cac uuc      158
Lys Asn Ile Val Thr Pro Arg Thr Asp Glu Asn Pro Val Val His Phe
 15                  20                  25 uuc aag aac auc gug acg cca cgc acc gau cau cau cau cac cau cac      206
Phe Lys Asn Ile Val Thr Pro Arg Thr Asp His His His His His His
 30                  35                  40                  45 uaa gcuugcggcc gcacucgagc accaccacca ccaccacuga gauccggcug            259
cuaacaaagc ccgaaaggaa gcugaguugg cugcugccac cgcugagcaa uaa            312
```

<210> SEQ ID NO 14
<211> LENGTH: 45
<212> TYPE: PRT
<213> ORGANISM: Artificial Sequence
<220> FEATURE:
<223> OTHER INFORMATION: Synthetic Construct

<400> SEQUENCE: 14

```
Met Ala Ser Ala Asp Glu Asn Pro Val Val His Phe Phe Lys Asn Ile
1               5                   10                  15

Val Thr Pro Arg Thr Asp Glu Asn Pro Val Val His Phe Phe Lys Asn
            20                  25                  30

Ile Val Thr Pro Arg Thr Asp His His His His His
        35                  40                  45
```

<210> SEQ ID NO 15
<211> LENGTH: 345
<212> TYPE: RNA
<213> ORGANISM: Artificial Sequence
<220> FEATURE:
<223> OTHER INFORMATION: Predicted mRNA sequence for PM2H expressed in
      pET21c
<220> FEATURE:
<221> NAME/KEY: RBS
<222> LOCATION: (57)..(87)
<223> OTHER INFORMATION: RBS covers a region starting from approximately
      15 nucleotides before the AUG start codon and ending at
      approximately 13 nucleotides after it.
<220> FEATURE:
<221> NAME/KEY: CDS
<222> LOCATION: (72)..(242)

<400> SEQUENCE: 15

```
gggggaauugu gagcggauaa caauuccccu cuagaaauaa uuuuguuuaa cuuuaagaag      60
gagauauaca u aug aaa uau aca uau ucu cug cac gug auc gug cag gcu      110
             Met Lys Tyr Thr Tyr Ser Leu His Val Ile Val Gln Ala
              1               5                  10 agc gcc gau gag aau ccg gug gug cac uuc uuc aag aac auc gug acg      158
Ser Ala Asp Glu Asn Pro Val Val His Phe Phe Lys Asn Ile Val Thr
 15              20                  25 cca cgc acc gau gag aau ccg gug gug cac uuc uuc aag aac auc gug      206
Pro Arg Thr Asp Glu Asn Pro Val Val His Phe Phe Lys Asn Ile Val
 30              35                  40                  45 acg cca cgc acc gau cau cau cau cac cau cac uaa gcuugcggcc           252
Thr Pro Arg Thr Asp His His His His His His
                 50                  55 gcacucgagc accaccacca ccaccacuga gauccggcug cuaacaaagc ccgaaggaa      312 gcugaguugg cugcugccac cgcugagcaa uaa                                 345

<210> SEQ ID NO 16
<211> LENGTH: 56
<212> TYPE: PRT
<213> ORGANISM: Artificial Sequence
<220> FEATURE:
<223> OTHER INFORMATION: Synthetic Construct

<400> SEQUENCE: 16

Met Lys Tyr Thr Tyr Ser Leu His Val Ile Val Gln Ala Ser Ala Asp
 1               5                  10                  15

Glu Asn Pro Val Val His Phe Phe Lys Asn Ile Val Thr Pro Arg Thr
             20                  25                  30

Asp Glu Asn Pro Val Val His Phe Phe Lys Asn Ile Val Thr Pro Arg
         35                  40                  45

Thr Asp His His His His His His
     50                  55

<210> SEQ ID NO 17
<211> LENGTH: 537
<212> TYPE: RNA
<213> ORGANISM: Artificial Sequence
<220> FEATURE:
<223> OTHER INFORMATION: Predicted mRNA sequence for UM2H expressed in
      pET21c
<220> FEATURE:
<221> NAME/KEY: RBS
<222> LOCATION: (57)..(87)
<223> OTHER INFORMATION: RBS covers a region starting from approximately
      15 nucleotides before the AUG start codon and ending at
      approximately 13 nucleotides after it.
<220> FEATURE:
<221> NAME/KEY: CDS
<222> LOCATION: (72)..(434)

<400> SEQUENCE: 17 gggggaauugu gagcggauaa caauuccccu cuagaaauaa uuuuguuuaa cuuuaagaag      60
gagauauaca u aug caa auc uuc guu aag acc cuc acu gga aag acc auc      110
             Met Gln Ile Phe Val Lys Thr Leu Thr Gly Lys Thr Ile
              1               5                  10 acu cuc gaa guu gag agu uca gau acc aua gac aau guu aag gca aag      158
Thr Leu Glu Val Glu Ser Ser Asp Thr Ile Asp Asn Val Lys Ala Lys
 15              20                  25 auu caa gac aag gaa gga auc cca ccu gac cag cag cgu cug auu uuu      206
Ile Gln Asp Lys Glu Gly Ile Pro Pro Asp Gln Gln Arg Leu Ile Phe
 30              35                  40                  45 gcu gga aag cag cug gag gau ggg cgu acc cuu gcu gau uau aac auc      254
Ala Gly Lys Gln Leu Glu Asp Gly Arg Thr Leu Ala Asp Tyr Asn Ile
```

-continued

| | | | | | | | | | | | | | | |
|---|---|---|---|---|---|---|---|---|---|---|---|---|---|---|
| | | | | 50 | | | | 55 | | | | 60 | | |
| cag | aag | gag | ucc | acc | cuc | cau | uug | gug | cuc | cgu | cuc | cgu | ggu | ggu | gcu | 302 |
| Gln | Lys | Glu | Ser | Thr | Leu | His | Leu | Val | Leu | Arg | Leu | Arg | Gly | Gly | Ala |
| | | | | 65 | | | | | 70 | | | | | 75 | |
| agc | gcc | gau | gag | aau | ccg | gug | gug | cac | uuc | uuc | aag | aac | auc | gug | acg | 350 |
| Ser | Ala | Asp | Glu | Asn | Pro | Val | Val | His | Phe | Phe | Lys | Asn | Ile | Val | Thr |
| | | | | 80 | | | | | 85 | | | | | 90 | |
| cca | cgc | acc | gau | gag | aau | ccg | gug | gug | cac | uuc | uuc | aag | aac | auc | gug | 398 |
| Pro | Arg | Thr | Asp | Glu | Asn | Pro | Val | Val | His | Phe | Phe | Lys | Asn | Ile | Val |
| | | | | 95 | | | | | 100 | | | | | 105 | |
| acg | cca | cgc | acc | gau | cau | cau | cau | cac | cau | cac | uaa | gcuugcggcc | | | | 444 |
| Thr | Pro | Arg | Thr | Asp | His | His | His | His | His | His | | | | | |
| 110 | | | | | | | 115 | | | | 120 | | | | | gcacucgagc accaccacca ccaccacuga gauccggcug cuaacaaagc ccgaaaggaa 504 gcugaguugg cugcugccac cgcugagcaa uaa 537

<210> SEQ ID NO 18
<211> LENGTH: 120
<212> TYPE: PRT
<213> ORGANISM: Artificial Sequence
<220> FEATURE:
<223> OTHER INFORMATION: Synthetic Construct

<400> SEQUENCE: 18

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Ala Ser Ala Asp
65                  70                  75                  80

Glu Asn Pro Val Val His Phe Phe Lys Asn Ile Val Thr Pro Arg Thr
                85                  90                  95

Asp Glu Asn Pro Val Val His Phe Phe Lys Asn Ile Val Thr Pro Arg
            100                 105                 110

Thr Asp His His His His His His
        115                 120

METHOD TO PRODUCE RECOMBINANT MBP8298 AND OTHER POLYPEPTIDES BY NUCLEOTIDE STRUCTURE OPTIMIZATION

CROSS-REFERENCE TO RELATED APPLICATIONS

This application claims the priority of U.S. Provisional Patent Application Ser. No. 61/073,369, filed Jun. 18, 2008, the entire content of which is incorporated herein by reference.

Sponsorship Statement

The present invention is sponsored by Isfahan Science and Technology Town (ISTT).

FIELD OF THE INVENTION

The invention relates to an improved method for the recombinant production in prokaryotes of polypeptide in general, and recombinant production of the therapeutic peptide MBP8298 in particular.

BACKGROUND OF THE INVENTION

Expression of recombinant proteins in prokaryotic systems such as in *Escherichia coli* is one of the most valuable tools in biotechnology both from the science and industry point of views. Yet, despite extensive research not every gene can be expressed successfully or efficiently in these organisms (Makrides, 1996; Morris and Geballe, 2000; Paulus et al, 2004; Zhang et al, 2006).

Following gene transcription, the expression process is largely controlled by the efficiency of the initiation, a phenomenon characterized by recruitment of mRNA and fMet-tRNA to the small subunit (30S) of the ribosome (Kozak, 1999; Laursen et al, 2005). On the mRNA molecule, two close nucleotide stretches have been long known for their critical role in specific interaction with the ribosome, the initiation codon and the Shine-Dalgarno (SD) sequence. The initiation codon is most often the tri-nucleotide AUG and conventionally stands at position +1 to +3 on the mRNA. The SD sequence is often a 5- to 13-nucleotide purine-rich motif with the core sequence of GGAGG that is optimally separated by 7±2 nucleotides upstream the initiation codon, i.e. SD sequence ends at position −8±2. Translation normally starts at position +1 (Ma et al, 2002; Sørensen and Mortensen, 2005). The initiation codon and SD sequence constitute the core of the ribosome binding site (RBS) on the mRNA 5′-end. Nevertheless, ribosome is known to embrace slightly larger areas of the mRNA during the translation process. Huttenhofer and Noller (1994) found that upon associates with a ribosome, a region spanning from positions approximately −35 to +20 of the mRNA is protected from a chemical modification. More recently Gulnara and coworkers (2001) employed X-ray crystallography to directly observe the path of mRNA inside the ribosome. Using a short synthetic mRNA with a SD sequence of AAGGAGG separated by 5 nt from the initiation ATG, they found that indeed only a region from nucleotides −15 to +16 of the mRNA is covered by the ribosome.

Amongst mRNA specifications that control the protein expressions, mRNA stability, codon usage, composition of the SD sequence and its distance from the initiation codon have received considerable attention from the scientists investigating the subject (for reviews see Makrides, 1996; Swartz, 2001; Sørensen and Mortensen; 2005). Nevertheless, many authors have also pointed to the intra-molecular Watson-Crick style bonds involving the SD sequences and the initiation codon as an additional determinant of the interaction between the mRNA and the 30S subunit and hence the protein expression level (Devlin et al, 1998; Makrides, 1996 and references therein; Helke et al, 1993 and references therein; Paulus et al, 2004). Composition of the downstream box (DB), that is sequences downstream the initiation codon, has also been implicated in protein expression levels most likely by controlling the mRNA secondary structure or folding (Sprengart et al, 1996; O'Connor et al, 1999; Stenström et al, 2001; Paulus et al, 2004). Since non-structural factors have been rather extensively studied they are often optimized in dedicated plasmid vectors used by experts and available through commercial suppliers. The less understood structural factors most relevant to this text, however, are discussed in the following Helke and coworkers (1993) were amongst the first authors who quantitated the mRNA structure stability in the ribosome binding regions and reported that strong base-pairing in this section tends to decrease the expression of proteins in *E. coli*. To this end they isolated varying lengths from the beginning of a highly expressible bacteriophage T7 gene and placed it upstream of a cloned mouse dihydrofolate reductase gene. Protein amounts expressed by the construct were then recorded. Using a minimum free energy algorithm, the authors predicted one folding for each selected stretch of deduced mRNA molecules and calculated its averaged free energy ($\Delta$G/nucleotide). By comparing the averaged free energies of different stretches of mRNA, they found that the region delimited by nucleotides −30 and +20 showed the best correlation with the expression of their model protein. These authors also reported that their method can predict the expression of many T7 genes but fails to predict the expression of nearly all non-T7 genes and suggested that other factors may control the expression of the later genes. Almost at the same time two other researchers, de Smit and van Duin (1990) who were working on recombinant expression in *E. coli* of the coat gene of bacteriophage MS2 reported a clear correlation between its translational efficiency and the stability of the mRNA initiation region secondary structure. Exploiting a natural hairpin structure involving 12 nucleotides in either sides of the initiation codon of their model gene and by careful site directed mutagenesis, they showed that loosening of the hairpin structures by as little as 1.4 kcal/mol could increase the gene's translational efficiency by an order of magnitude. These authors, too, used a minimum energy algorithm to predict the structure of the isolated stretch of the mRNA and its free energy although they used the total free energy of the stretch not the averaged ($\Delta$G/nucleotide) value. De Smit and van Duin argued that concentration of the 30S subunit and its affinity for the mRNA's ribosome binding site, on one side, and the strength of the regional mRNA internal structure, on the other side, determines how many of the ribosomes can successfully interact with the mRNA. These authors suggest that ribosomes only bind to single-stranded RNA (which is in equilibrium with the folded form) and that loosening of the mRNA secondary structure in the RBS pushes the equilibrium towards more unfolded RBS and hence higher ribosome association and subsequent expression (de Smit and van Duin, 1990).

More recently, Voges and coworkers (2004) used a comprehensive statistical approach to investigate the effect of mRNA sequences downstream the initiation codon in a cell-free protein synthesis system (RTS 100 *E. coli* HY Kit, Roche Applied Science) based on the T7 promoter/terminator. These authors inserted a versatile array of 39-nucleotide stretches in position +4 of a GFP expression cassette and assessed the GFP expression levels in the new constructs. This was then correlated with up to 356 calculated sequence attributes including G+C contents and mRNA secondary structures in the first 300 nucleotides. However, unlike the previous studies emphasis were placed on the probability of individual nucleotides participating in base pair formation and on positions of local stem loops (as well as their energy contents). Voges and coworkers reported that the most significant factor correlated with expression levels in their experiment was the mRNA inverse G+C content, in particular in the third bases of codons 2 to 7. Nevertheless, the authors pointed out that this finding was in contrast with that in the innate *E. coli* highly expressible genes. These authors also reported that higher base pair probabilities downstream of the initiation point, in particular in bases +3 to +25 (almost corresponding to codons 1 to 9), were correlated with lower expression levels. The authors concluded that accessibility of unpaired nucleotides bases in this region encouraged translational efficiency. Attempts to predict protein expressions based on the above data was meet with only moderate success as the authors reported an adjusted correlation coefficient (R-square) of only 0.42 (Voges et al, 2004). A web-based application, ProteoExpert, developed based on this analysis and dedicated to optimized protein expression in cell-free systems is available biomax-.com. A patent application related to this method was also found in the USPTO website (20060024679).

The controversy on the exact position and size of the region that controls the expression of recombinant proteins in prokaryotic cells has been a common theme in other reports too. Wang and coworkers (1994) reported that they analyzed a stretch of mRNA comprising 5 nucleotides upstream the SD to 40 nt downstream of AUG and discovered that potential secondary structures in this region markedly hamper the expression of their model protein, prochymosin. The minimum expression of prochymosin was obtained with the free energy of −11 kcal/mol in this region whereas smaller $\Delta G$ values down to −4 or −4.43 increased the expression up to an impressive 39% of the total cell proteins. Another authors, Cèbe, and Geiser (2006), used an experimental system based on the genes for sphingosine kinase 1 and the sclerostin protein to find out that the 5' region of the mRNA spanning from the first A of the SD sequence to nucleotide +72 may be used to predict protein expression levels. They suggested that if the total $\Delta G$ in this region is above −4 to −4.78 kcal/mol, the mRNA will be effectively translated. On the other hand, stronger structure in this region is inhibitory to translation although this may be reversed by silent mutations in the region that disrupts the existing base pairs. More recently, Care et al (2007) estimated the free energy of the −70 to +96 region of the mRNA to optimize the expression of proteins. They reported that by mutating nucleotides in the −17 to +9 regions they reduced the free energy content of the crucial +70/+96 region and enhanced the expression of 8 out of 9 proteins that they used in their experiment. A web-based application, ExEnSo, developed based on this concept is available exenso.afmb.univ-mrs.fr.

Formation of intra-molecular bonds in mRNA secondary structure may be predicted using a variety of software exemplified by Rdfolder rna.cbi.pku.edu.com, Vienna RNA secondary structure server tbi.univie.ac.at, Sfold sfold.wadsworth.org, CONTRAfold contra.stanford.edu and mfold. Amongst these, the Vienna RNA secondary structure server appears to have been used in more articles (Voges et al, 2004; Cèbe, and Geiser, 2006; Zhang et al, 2006) although the algorithm of mfold was also successfully employed (Paulus et al, 2004).

Since mfold readily generates more than one structures with close minimum energies (known as optimal and sub-optimal structures) it is perhaps more appropriate for prediction of secondary structures in the dynamic mRNA molecules. This may be even more applicable considering concurrent translation and transcription in prokaryotes. The number of minimum-free-energy structures generated by mfold may be adjusted by the sub-optimality value but it is 5% by default (Zuker, 2003). The latest version of mfold (version 3.2) that uses improved thermodynamic values is used in the research presented throughout this application.

MBP8298 also mentioned in the following paragraphs is a 17-amino acid peptide that has been shown to constitute a novel treatment in management of multiple sclerosis. The peptide corresponds to amino acids 82 to 98 of the human myelin basic protein (MBP) and is presently produced by chemical synthesis only (Warren at al, 2006). (Paulus at al, 2004)

SUMMARY OF THE INVENTION

The present invention provides a novel method to estimate the efficiency of recombinanat protein expression in prokariotic cells. It also provides a novel method to optimize encoding DNA sequences of polypeptides in order to maximize their expression in heterologous hosts.

The invention provides novel materials and methods for recombinant production of hard-to-express polypeptides, exemplified by the MBP8298 therapeutic peptide. Novel constructs containing multiple copies of a transcription unit comprising recombinant DNA sequence which encodes MBP8298 are also provided. Furthermore, bacterial cell lines harboring vectors that contain these constructs are provided. The bacterial cell lines are capable of expressing MBP8298 encoded by the transcription units.

It was shown that MBP8298 fusion protein is effectively made in *Escherichia coli* and cleaved by Asp-N endoproteinase. The peptide manufactured in this way was shown to have the same characteristics expected for authentic MBP8298. Thus, the invention provides genuine recombinant MBP8298 peptides.

The invention provides recombinant DNA vector constructs suitable for introduction into a bacterial host in which the construct includes a coding sequence for a fusion protein having: (a) an optional expression enhancer encoding DNA sequence at the 5' end; (b) at least one MBP8298 encoding DNA sequence; and (c) an optional 3'-end peptide tag encoding DNA sequence that starts with an aspartate encoding DNA sequence. The invention further provides an encoded MBP8298 peptide that may be used for treatment of multiple sclerosis. *Escherichia coli* host cells transformed with vector constructs according to the invention are provided.

The invention provides ways for bacterial production of fusion proteins and MBP8298 peptides by culturing the bacterial host cells that carry the vector construct encoding the fusion protein containing MBP8298 peptide-, expression enhancer peptide-, peptide tag starting with aspartate-encoding sequences, by isolating the expressed fusion protein, by cleaving the expressed fusion protein to release the MBP8298 peptide, and by isolating the MBP8298 peptide. We have provided the methods for bacterial production of the fusion proteins. This includes culturing a bacterial host cell transformed with a vector construct encoding the fusion protein, isolating the expressed fusion protein, cleaving the MBP8298 peptide from the fusion protein, and purifying the MBP8298 peptide. Fusion protein products of such processes are also provided. Furthermore, MBP8298 peptide products of processes according to the invention are provided.

DETAILED DESCRIPTION

Figure 1:
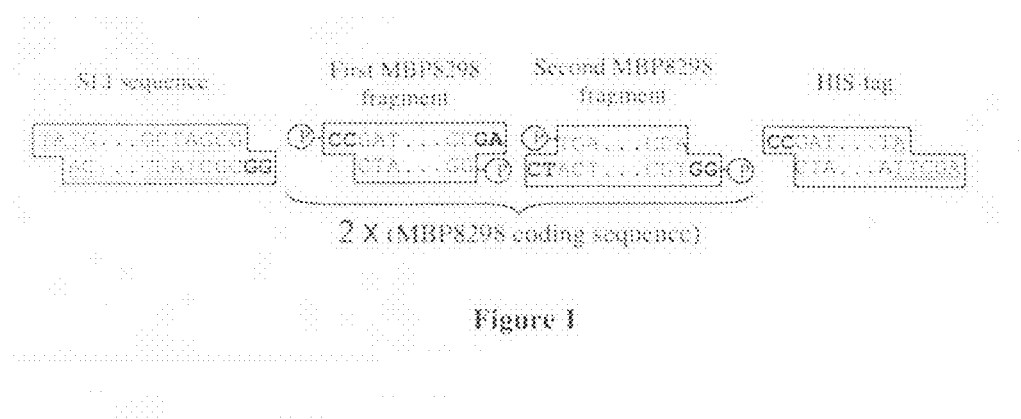
FIG. 1: The PM$_2$H recombinant coding sequence comprising of a SLI sequence, two MBP8298 encoding DNA sequences and a HIS-tag encoding DNA sequence.

The present invention is based on a method to predict the expression efficiency of the encoding nucleotide sequences of polypeptides. The encoding nucleotides are then optimized to maximize their recombinant expression. An embodiment of this method is the production of the MBP8298 peptide that is explained in details hereinafter. The embodiment provides methods to predict and optimize expression of MBP8298-containing fusion proteins, compositions of such fusion proteins, scheme to release MBP8298 from such proteins and recombinant methods to make related encoding DNA sequences.

The expression of MBP8298 therapeutic peptide may be achieved as fusion proteins that contain at least one MBP8298 sequence, one expression enhancer sequence and at least one amino acid cleavage site sequence located between the peptides as well as between the peptide and the expression enhancer. The fusion protein may also contain one or more peptide tag (normally attached via at least one amino acid cleavage site to the C-terminal) for facilitated purification. The invention provides a method for the recombinant production of such fusion proteins encoding one or more MBP8298. The recombinant MBP8298 peptides of the invention are cleaved from each other and from the fusion protein at the cleavage sites in the fusion protein. Since MBP8298 peptide contains one single aspartate residue at its N-terminal end, in its simplest and most preferred form, the peptide is cut out of the fusion protein using endoproteinase Asp N. In this way no additional residues need to be engineered between MBP8298 tandem repeats or between MBP8298 and the expression enhancer. The C-terminal peptide tag (if present) will also need to start with a cleavable aspartate residue.

Such MBP8298-containing fusion proteins can be expressed in large amounts without detectable proteolysis of the target peptide, MBP8298. As such, this recombinant MBP8298 may be readily purified and used for treatment of multiple sclerosis.

According to the invention a variety of expression enhancers such as ubiquitin-encoding sequence may be used by recombinant DNA techniques to increase the expression of the MBP8298-containing fusion proteins. When present on the N-terminal of fusion proteins, expression enhancers increase expression of the proteins and protect MBP8298 from proteolytic degradation during production.

An advantage provided by present invention is the ability to produce MBP8298 efficiently and economically from bacterial host cells. Additional advantages include the ability to obtain homogeneous peptide in large amounts via methods that are amenable to scale-up.

MBP8298 as used herein refers to a 2012.05-Da peptide fragment (monoisotopic mass) corresponding to the amino acid 82 to 98 of the human myelin basic protein (MBP) with the sequence of DENPVVHFFKNIVTPRT (SEQ ID NO: 1).

As used herein "expression prediction" refers to the analysis of the sequence and structure of recombinant protein encoding mRNA sequences by bioinformatics methods in a way that expression of the recombinant protein is predicted. According to the invention, expression prediction is based on the analysis of the 5'-end of the encoding mRNA. While the length of the required 5'-end segment is flexible and may range from 100 to 200, it was found that often 130 to 150 nucleotides provide the best prediction. For improved precision, 3 different 5' segments of said mRNA comprising 130, 140 and 150 nucleotides are used and results are averaged later.

For each mRNA segment all the likely secondary structures within a minimum of approximately 7% from the global minimum free energy of said mRNA (7% sub-optimality) are computed. Although it is possible to use higher sub-optimality percentage, quite often it was found that 5-7% sub-optimality provides enough precision for the final prediction while keeping the calculations to a minimum. The probability of forming each structure is then calculated based on the Boltzmann distribution and by using equation 1 in which P is the probability of the structure, $K_f$ is the equilibrium constant of helix formation and Q or partition function is the sum of probability of all possible structures, s.

$$P = \frac{Kf}{Q} \qquad \text{Equation 1}$$

$K_f$ may be calculated following equation 2 where $\Delta G$ is the structure minimum free energy (kcal/mole), T is the absolute temperature in Kelvin (K) and k is the Boltzmann gas constant (0.001986266 kcal/mole/degree K).

$$K_f = \exp\left(\frac{-\Delta G}{Tk}\right) \qquad \text{Equation 2}$$

Q, on the other hand, may be calculated by equation 3 in which $\Delta G_S$ is the minimum free energy (kcal/mole) of all possible structures, s. As before, T is the absolute temperature and k is the Boltzmann gas constant. Most often structures obtained by 5 to 10% sub-optimality account for >90% to >99% of all probable structures respectively.

$$Q = \sum_{S}\left[\exp\left(\frac{-\Delta G_S}{Tk}\right)\right] \qquad \text{Equation 3}$$

For each predicted structure the free energy of the translation initiation region (TIR) defined as the sequences starting from approximately nucleotide −15 and ending with approximately nucleotide +16, is calculated. According to the invention regardless of the mRNA structure, only the free energy of TIR is correlated with the expression level of recombinant proteins. The fraction of unfolded TIR, being the only form that may successfully interact with ribosome, is calculated based on equation 4 in which $F_u$ is the fraction of unfolded TIR and $K_f$ is the equilibrium constant of helix formation.

$$F_u = \frac{1}{K_f + 1} \qquad \text{Equation 4}$$

Using both equations 2 and 4, it is concluded that $F_u$ may be calculated based on equation 5 in which $\delta G_{TIR}$ is the free energy of TIR (kcal/mole), T is the absolute temperature and k is the Boltzmann gas constant.

$$F_u = \frac{1}{\exp\left(\frac{-\delta G_{TIR}}{Tk}\right) + 1} \qquad \text{Equation 5}$$

For each mRNA segment the probability of unfolded TIR ($P_u$) is calculated by equation 6 in which $P_S$ and $F_{uS}$ are respectively the probability of the mRNA structure and the fraction of unfolded TIR of all possible structures, s, for said mRNA segment.

$$P_u = \sum_s P_S \times F_{uS} \qquad \text{Equation 6}$$

The $P_u$ values obtained for the three 5' segment are simply averaged to obtain averaged probability of unfolded TIR ($\overline{Pu}$).

We found that the expression levels of recombinant proteins have a sigmoid relationship with the averaged $P_u$ of these proteins. Hence expression of the recombinant protein may be estimated according to equation 7 in which E is expression measured as the fraction of the maximum expressibility of said protein, $\overline{Pu}$ is averaged probability of unfolded TIR. A is a system-dependent variables that depends on the cell and the protein involved. A equals to approximately 0.009 for systems that we examined. E ranges from 0 to 1 for minimum and maximum expressions, respectively.

$$E = \frac{Pu}{Pu + A} \qquad \text{Equation 7}$$

For simplicity we also prepared Table 1 in which averaged probability of unfolded TIR may be used to estimate expected expression shown as the level of expression compared to the total cell proteins.

TABLE 1

| Average probability of unfolded TIR $\overline{Pu}$ | Expected expression efficiency |
|---|---|
| <$10^{-6}$ | Nil |
| $10^{-6}$-$10^{-4}$ | Very low |
| $10^{-4}$-$10^{-4}$ | Low |
| $10^{-4}$-$10^{-2}$ | Intermediate |
| $10^{-2}$-$10^{-1}$ | High |
| >$10^{-1}$ | Very high |

The novelty and strength of the present method is in using more than one mRNA structure to assess the expression level. The method also separates folding region from ribosome interaction region and uses two different criteria to select and analyze each. The method is based on the mRNA 5' region, which is most likely to play a key role in the coupled prokaryotic translation/transcription, but it only uses the free energy of the region that interacts with the 30S ribosome to assess this interaction. Application of different length of the mRNA is also reminiscent of the growing nascent mRNA while it is translated. The method is exclusively intended for prokaryotes and likely applies only if other factors, such as the mRNA stability, codon usage, composition of the SD sequence and its distance from the initiation codon are not inhibitory to the expression.

As used herein "sequence optimization" refers to the analysis and optimization of recombinant protein encoding DNA sequences based on expression prediction in a way that expression of the recombinant protein would increase. The DNA sequence optimization of the invention is carried out at two levels as follow:

1—The prokaryotic rare codons as indicated by the organism codon usage are not used when possible. Consecutive rare codons and rare codons close to the initiation codons are specially important to avoid.

2—Unfavorable mRNA secondary structures that could decrease the translation of recombinant genes be avoided. To optimize an unfavorable structure, base-pair forming nucleotides involving the TIR are modified in a way that the structure is disrupted but the amino acids are not changed when possible. Alternatively, nucleotides outside TIR may be modified in way that they draw the strong base pair formation away from the TIR.

As used herein a "transformed bacterial host cell" refers to a bacterial cell that contains recombinant genetic material or a bacterial cell that contains genetic material required for expression of a recombinant product. The genetic material may be introduced by any method known in the art including transformation, transduction, electroporation and infection.

As used herein, a "vector construct" refers to plasmid DNA that contains recombinant genetic material which may encode a recombinant product(s) and may be capable of autonomous replication in bacteria.

"Recombinant coding sequence" (CDS) as used herein refers to a recombinant genetic sequence which encodes a recombinant product. Once placed inside a vector construct by recombinant DNA techniques, the CDS may be transcribed into mRNA which is then translated into the a recombinant product by host ribosomes.

"Expression enhancer" as used herein refers to a sequence that is fused, by recombinant DNA techniques, to the upstream of the recombinant product and confers high level-expression to the linked protein or peptide. Preferred expression enhancers may also induce formation of inclusion bodies (IBs) that force the fusion protein to be deposited in insoluble IBs which may in turn facilitate their isolation from the host.

"Amino acid cleavage site" as used herein refers to an amino acid or amino acids that serve as a recognition site for a chemical or enzymatic reaction such that the peptide chain is cleaved at that site by the chemical agent or enzyme. Preferred amino acid cleavage site for MBP8298 is aspartate that may be cleaved at its N-terminal by proteases known as endoproteinase Asp-N.

Other aspects and advantages of the present invention will be explained in more details in the following illustrative examples on expression of MBP8298 wherein Example 1 addresses design of the fusion protein encoding DNA segments, example 2 addresses structure prediction and optimization process of fusion protein encoding mRNA sequences, example 3 addresses assembling of fusion protein expression vector constructs, example 4 addresses expression of recombinant fusion proteins, and example 5 addresses cleavage of MBP8298 peptide from a fusion protein.

EXAMPLE 1

Design of the Fusion Protein Encoding DNA Segments

In their complete forms, fusion protein encoding DNA sequences were made of 3 sections including (a) an optional expression enhancer encoding DNA sequence, (b) MBP8298 encoding DNA sequences, and (c) an optional His-tag encoding DNA sequence. These sections were fabricated separately and then assembled together. Design of the sections are explained in the following paragraphs:

a. Expression Enhancer Encoding DNA Sequences

Two different expression enhancer encoding DNA sequences were made, a plant ubiquitin encoding DNA sequence and a stem-loop inducing (SLI) sequence.

The plant ubiquitin encoding DNA sequence was isolated from *Medicago truncatula* (Mt) genome. DNA from 20 mg plant leaves was amplified in a PCR reaction containing 10 pmol of ubiquitin left primer (TATACATATGCAAATCT-TCGTTAAGACCC) (SEQ ID NO: 2) and 10 pmol of ubiquitin right primer (ATTAGCTAGCACCACCACGGAG) (SEQ ID NO: 3) following the standard protocol. Underlined in the left primer is a NdeI site and in the right primer is a NheI site. Sequence of the Mt-ubiquitin encoding DNA sequence, confirmed by sequencing, is shown next. In this sequence NdeI and NheI sites, respectively at the beginning and end of the sequence, are underlined.

Nucleotide sequence of the *Medicago truncatula* ubiquitin (SEQ ID NO: 4):

CATATGCAAATCTTCGTTAAGACCCTCACTGGAAAGACCATCACTCTCG

AAGTTGAGAGTTCAGATACCATAGACAATGTTAAGGCAAAGATTCAAG

ACAAGGAAGGAATCCCACCTGACCAGCAGCGTCTGATTTTTGCTGGAA

AGCAGCTGGAGGATGGGCGTACCCTTGCTGATTATAACATCCAGAAGG

AGTCCACCCTCCATTTGGTGCTCCGTCTCCGTGGTGGTGCTAGC

The SLI sequence, with an ATG at the beginning and a NheI site at the end, was intended to form an internal stem-loop with −11.8 kcal/mol free energy at position +18 of the ensuing mRNA. By itself the stem-loop would have been strong enough to stop the ribosome binding and hence expression should the TIR extends behind its boundaries as defined in the invention. The stem-loop inducing sequence was synthetically fabricated from two single stranded oligonucleotides with the following sequences:

1-
5'TATGAAATATACATATTCTCTGCACGTGATCGTGCAGGCTAGCG3'
(SEQ ID NO: 6)

2-
5'GGCGCTAGCCTGCACGATCACGTGCAGAGAATATGTATATTTCA3'
(SEQ ID NO: 7)

The oligonucleotide strands were annealed by heating to 94° C. in the annealing buffer (200 mM TRIS, pH 7.8, 50 mM MgCl$_2$, 50 mM DTT and 2.5 mM ATP) followed by cooling to 25° C. in 99 minutes. The resulting double stranded fragment had a NdeI site on the left (double underlined), a NheI site near the right end (underlined) and a 5'-end GG overhang on the right (bold letters).

b. MBP8298 Encoding DNA Sequences

Two slightly different fragments of MBP8298 encoding DNA sequences that could ligate alternatively in a head-to-toe manner, forming sequence concatamers of even numbers, were synthesized. The first fragment (M1) was fabricated by annealing two 5'-phosphorilated oligonucleotide strands with the following sequences:

1-
5'(P)CCGATGAGAATCCGGTGGTGCACTTCTTCAAGAACATCGTGACGC

CACGCACCGA3' (SEQ ID NO: 8)

2-
5'(P)GGTGCGTGGCGTCACGATGTTCTTGAAGAAGTGCACCACCGGATT

CTCATC3' (SEQ ID NO: 9)

The oligonucleotide strands were annealed as explained above. The resulting double stranded fragment had a 5'-end CC overhang (bold letters) on the left and a 3'-end GA overhang (bold letters) on the right.

The second fragment (M2) was also fabricated by annealing two 5'-phosphorilated oligonucleotide strands with the following sequences:

5'(P)TGAGAATCCGGTGGTGCACTTCTTCAAGAACATCGTGACGCCACG

CA3' (SEQ ID NO: 10)

5'(P)GGTGCGTGGCGTCACGATGTTCTTGAAGAAGTGCACCACCGGATT

CTCATC3' (SEQ ID NO: 9)

The oligonucleotides were again annealed as explained above. The resulting double stranded fragment had a left side 3'-end TC overhang (bold letters) and a right side 5'-end GG overhang (bold letters).

Because of the phenomenon of codon degeneracy the above composition of MBP8298 encoding DNA sequence is not the only possible composition. To arrive at this composition a tentative sequence was produced and the ensuing mRNA sequence was subjected to the sequence optimization scheme explained earlier. If the structure was found to be unfavorable, one or more nucleotides in the sequence were replaced with other ones and the structural analysis was repeated until an optimum structure was found. Method to predict structures and how to distinguish suitable structures from unsuitable ones are explained in Example 2.

c. His-Tag Encoding DNA Sequence

His-tag encoding DNA sequence was also fabricated from two single stranded oligonucleotides with the following sequences:

1- 5'CCgATCATCATCATCACCATCACTA3'
(SEQ ID NO: 11)

2- 5'AgCTTAgTgATggTgATgATgATgATC3'
(SEQ ID NO: 12)

The oligonucleotide strands were annealed as explained above. The resulting double stranded sequence had a left side 5'-end CC overhang (bold letters) and a HindIII site on the right (double underlined).

FIG. 1 depicts the way that one SLI sequence, two MBP8298 encoding DNA sequences and one His-tag encoding DNA sequence were ligated to form a recombinant coding sequence (CDS) dubbed PM$_2$H. In this CDS first and second fragments of MBP8298 encoding DNA sequences ligate alternatively, forming n tandem repeats of 2 MBP8298 encoding DNA sequences. Double underlined nucleotides in the SLI sequence and the His-tag encoding DNA sequence highlight the positions of NdeI and HindIII restriction sites respectively. The single underlined nucleotides in the SLI sequence denote the NheI restriction site.

In the other variant, named UM$_2$H, the SLI sequence was replaced by the ubiquitin encoding DNA sequence. In the third variant, M$_2$H, only two MBP8298 encoding DNA sequences and one HIS-tag encoding DNA sequence were ligated, leaving out any expression enhancer (i.e. SLI sequence and ubiquitin encoding DNA sequence) in the final CDS.

EXAMPLE 2

Structure Prediction and Optimization Process of Fusion Protein Encoding mRNA Sequences For sequence optimization, mRNA sequences of the MBP8298-containing CDS described in Example 1 were to be analyzed to predict their secondary structures and therefore to predict if they may be over-expressed in *E. coli*. To this end, first the mRNA sequences of the recombinant genes when inside the vector construct were predicted by taking into account the CDS ligation sites as well as the vector transcription initiation/stop points. Assuming that the genes are in pET21c vector, the mRNA molecules will have the follow sequences:

1—For M$_2$H comprising of two MBP8298 and a His-tag (SEQ ID NO: 13)

GGGGAAUUGUGAGCGGAUAACAAUUCCCCUCUAGAAAUAAUUUUGUUU

AACUUUAAGAAGGAGAUAUACAUAUGGcuagcgccgaugagaauccggug gugcacuucuucaagaacaucgugacgccacgcaccgauGAGAAUCCGGU GGUGCACUUCUUCAAGAACAUCGUGACGCCACGCAccgaucaucaucauc accaucacuaAGCUUGCGGCCGCACUCGAGCACCACCACCACCACCACUG

AGAUCCGGCUGCUAACAAAGCCCGAAAGGAAGCUGAGUUGGCUGCUGCCA

CCGCUGAGCAAUAA (underlined sequences are NheI and HindIII restriction sites respectively)

2—For PM$_2$H comprising of a modified SLI sequence, two MBP8298 and a His-tag (SEQ ID NO: 15)

GGGGAAUUGUGAGCGGAUAACAAUUCCCCUCUAGAAAUAAUUUUGUUU

AACUUUAAGAAGGAGAUAUACAuaugaaauauacauauucucugcacgug aucgugcaggcuagcgCCGAUGAGAAUCCGGUGGUGCACUUCUUCAAGAA CAUCGUGACGCCACGCACCGAugagaauccgguggugcacuucuucaaga -continued acaucgugacgccacgcaCCGAUCAUCAUCAUCACCAUCACUAagcuugc ggccgcacucgagcaccaccaccaccaccacugagauccggcugcuaaca aagcccgaaaggaagcugaguuggcugcugccaccgcugagcaauaa (underlined sequences are NdeI, NheI and HindIII restriction sites respectively)

3—For UM$_2$H comprising of a plant ubiquitin, two MBP8298 and a His-tag (SEQ ID NO: 17)

GGGGAAUUGUGAGCGGAUAACAAUUCCCCUCUAGAAAUAAUUUUGUUU

AACUUUAAGAAGGAGAUAUACAuaugcaaaucuucguuaagacccucacu ggaaagaccaucacucucgaaguugagaguucagauaccauagacaaugu uaaggcaaagauucaagacaaggaaggaaucccaccugaccagcagcguc ugauuuuugcuggaaagcagcuggaggaugggcguacccuugcugauuau aacauccagaaggaguccacccuccauuuggugcuccgucuccguggugg ugCUAGCGCCGAUGAGAAUCCGGUGGUGCACUUCUUCAAGAACAUCGUGA CGCCACGCACCGAugagaauccgguggugcacuucuucaagaacaucgug acgccacgcaCCGAUCAUCAUCAUCACCAUCACUAagcuugcggccgcac ucgagcaccaccaccaccaccacugagauccggcugcuaacaaagcccga aaggaagcugaguuggcugcugccaccgcugagcaauaa (underlined sequences are NdeI, NheI and HindIII restriction sites respectively)

In all the above sequences the Shine-Dalgarno sequences (AAGGAG) and the initiation codons (AUG) are in bold letters whereas engineered restriction sites are underlined. To distinguish discrete fragments that are assembled into the above mRNA sequences, these fragments are printed in alternative capital and small letters. The actual process involved in the assembly of the DNA fragments will be explained in Example 3.

For each of the three mRNA sequences, segments consisting the first 130, 140 and 150 nucleotides were analyzed for mRNA folding structures with a sub-optimality of 7%. A maximum of 6 structures (S1 to S6) were obtained for each segment. Factors explained in the previous paragraphs were then calculated sequentially Results for M$_2$H, PM$_2$H and UM$_2$H are shown in Tables 2, 3 and 4 respectively. In all these tables $\Delta G$, P, $\delta G_{TIR}$, and Fu, as defined in DETAILED DESCRIPTION, are individually shown for the 130-, 140- and 150-nucleotide segments. In the last column on the right the average probability of unfolded TIR (Pu) for each segment is presented. The global average probability of unfolded TIR for each sequence is shown at the bottom right. By comparing the global averages with the values shown in Table 1, it is predicted that expression efficiencies for M$_2$H, PM$_2$H and UM$_2$H are respectively nil, high and high. Alternatively, Equation 7 may be used to obtain a numerical estimate of the expression (as fraction of the maximum potential expression) or E. To this end E for M2H, PM2H and UM2H are 0%, 82% and 89% respectively. These predictions will be shown in Example 4 and FIG. 2 to be in fact correct.

TABLE 2

| Sequence length | Variable | Minimum-free-energy secondary structures | | | | | | Pu |
|---|---|---|---|---|---|---|---|---|
| | | S1 | S2 | S3 | S4 | S5 | S6 | |
| 130 | ΔG | −37.2 | −36.9 | −36.7 | −36.6 | −36.5 | −34.7 | 4.13E−09 |
| | P | 36.0% | 22.1% | 16.0% | 13.6% | 11.6% | 0.6% | |
| | δG | −12 | −14.3 | −12.8 | −11.4 | −12.4 | −9.5 | |
| | Fu | 3.47E−09 | 8.30E−11 | 9.47E−10 | 9.19E−09 | 1.81E−09 | 2.01E−07 | |
| 140 | ΔG | −37.8 | −37.3 | −37.2 | −36.9 | −36.6 | −36.5 | 1.27E−09 |
| | P | 43.1% | 19.2% | 16.3% | 10.0% | 6.2% | 5.2% | |
| | δG | −13.8 | −13.8 | −12 | −14.3 | −11.4 | −13.8 | |
| | Fu | 1.87E−10 | 1.87E−10 | 3.47E−09 | 8.30E−11 | 9.19E−09 | 1.87E−10 | |
| 150 | ΔG | −44 | −43.7 | −43.5 | −43.4 | −42.9 | | 3.67E−10 |
| | P | 38.4% | 23.6% | 17.1% | 14.5% | 6.4% | | |
| | δG | −13.3 | −15.6 | −13.9 | −12.7 | −13.7 | | |
| | Fu | 4.21E−10 | 1.01E−11 | 1.59E−10 | 1.11E−09 | 2.20E−10 | | |
| Average | | | | | | | | 1.92E−9 |

TABLE 3

| Sequence length | Variable | Minimum-free-energy secondary structures | | | | | | Pu |
|---|---|---|---|---|---|---|---|---|
| | | S1 | S2 | S3 | S4 | S5 | S6 | |
| 130 | ΔG | −35.5 | −35.4 | −35.2 | −34.8 | −34.2 | −33.9 | 1.25E−01 |
| | P | 34% | 29% | 21% | 11% | 4% | 2% | |
| | δG | −0.5 | −7.9 | −7.7 | −8.4 | −8.2 | 1.1 | |
| | Fu | 3.08E−01 | 2.70E−06 | 3.73E−06 | 1.20E−06 | 1.66E−06 | 8.56E−01 | |
| 140 | ΔG | −40.2 | −39.8 | −39.3 | −39.3 | −38.5 | −38.2 | 3.71E−04 |
| | P | 48% | 25% | 11% | 11% | 3% | 2% | |
| | δG | −6.2 | −4.4 | −4.4 | −5.3 | −4.4 | −4.2 | |
| | Fu | 4.26E−05 | 7.90E−04 | 7.90E−04 | 1.83E−04 | 7.90E−04 | 1.09E−03 | |
| 150 | ΔG | −46.2 | −45.7 | −45.7 | −44.9 | −43.3 | −43 | 2.94E−04 |
| | P | 49% | 22% | 22% | 6% | 0% | 0% | |
| | δG | −9.1 | −9.1 | −4.4 | −9.1 | −6.2 | −1.9 | |
| | Fu | 3.84E−07 | 3.84E−07 | 7.90E−04 | 3.84E−07 | 4.26E−05 | 4.38E−02 | |
| Average | | | | | | | | 4.17E−02 |

EXAMPLE 3

Assembly of Fusion Protein Expression Vector Constructs

1. Bacterial Expression Vector Construct: pET21c-PM$_2$H

A bacterial expression vector which would encode a MBP8298-containing fusion protein was constructed. This vector contained a SLI sequence linked to 2 MBP8298 encoding DNA sequences and a His-tag encoding fragment.

The amount of 0.07 pico mol pET21c vector digested with HindIII and NdeI restriction enzymes were mixed with 0.7 pico mol of His-tag DNA fragment and 0.7 pico mol of SLI DNA fragment and ligated for 2 hr at 22° C. using 5u of T$_4$ DNA

TABLE 4

| Sequence length | Variable | Minimum-free-energy secondary structures | | | | | | Pu |
|---|---|---|---|---|---|---|---|---|
| | | S1 | S2 | S3 | S4 | S5 | S5 | |
| 130 | ΔG | −31 | −30.4 | −29.7 | −29 | −28.9 | | 3.76E−02 |
| | P | 64% | 24% | 8% | 2% | 2% | | |
| | δGRBS | −2.3 | −3.4 | −2.3 | 0.6 | −1.4 | | |
| | Fu | 2.34E−02 | 3.99E−03 | 2.34E−02 | 7.26E−01 | 9.34E−02 | | |
| 140 | ΔG | −31 | −30.8 | −30.7 | 29.4 | 29.2 | | 8.02E−03 |
| | P | 43% | 31% | 26% | 0% | 0% | | |
| | δGRBS | −4 | −3.4 | −2.3 | 0.6 | 0.8 | | |
| | Fu | 0.15% | 0.40% | 2.34% | 72.59% | 78.56% | | |
| 150 | ΔG | −34.6 | −34.2 | −34.1 | −32.5 | −32.5 | −32.2 | 1.78E−01 |
| | P | 49% | 25% | 22% | 2% | 2% | 1% | |
| | δGRBS | −1.7 | −1.6 | 0 | 1.9 | 0 | −2.9 | |
| | Fu | 5.95E−02 | 6.93E−02 | 5.00E−01 | 9.56E−01 | 5.00E−01 | 8.95E−03 | |
| Average | | | | | | | | 7.47E−02 | ligase. Next, 4 pico mol of each of MBP8298 DNA fragments M1 and M2 were added to the mixture and the ligation reaction continued for a further 1 hr at 22° C.

2. Bacterial Expression Vector Construct: pET21c-UM$_2$H

This bacterial expression vector was constructed from pET21c-PM$_2$H vector and in every aspect resembled that except it contained a ubiquitin encoding DNA sequence instead of the SLI fragment.

pET21c-PM$_2$H vector was digested with NheI and NdeI restriction enzymes, dephosphorilated with Calf Intestinal Alkaline Phosphatase and heated to 80° C. for 25 minutes to deactivate the enzymes. The amount of 0.03 pico mol of the linear vector was ligated with 0.1 pico mol of ubiquitin encoding DNA fragment already digested with NheI and NdeI restriction enzymes as above.

3. Bacterial Expression Vector Construct: pET21c-M$_2$H

This bacterial expression vector was also constructed from pET21c-PM$_2$H vector and resembled that but it contained only 2 MBP8298 encoding DNA sequences and a His-tag encoding fragment.

pET21c-PM$_2$H vector was digested with HindIII and NheI restriction enzymes, and after resolving on 1.2% TBE-Agarose gel, the M$_2$H fragment was purified. Parallel to this, pET21c vector was also digested with HindIII and NheI restriction enzymes, dephosphorilated with Calf Intestinal Alkaline Phosphatase and heated to 80° C. for 25 min. Equivalent to 0.1 pico mol of the purified fragment was ligated with 0.03 pico mol of the linear pET21c using T$_4$ DNA ligase.

EXAMPLE 4

Expression of Recombinant Fusion Proteins

1. Production of Transformed Hosts

The following expression vector constructs as described in Example 3 were used:
a—pET21c-M$_2$H
b—pET21c-PM$_2$H
c—pET21c-UM$_2$H Expression vector constructs were separately transformed into *E. coli* BL21 (DE3) by the calcium chloride protocol known in the art.

2. Small Scale Production

Figure 2:
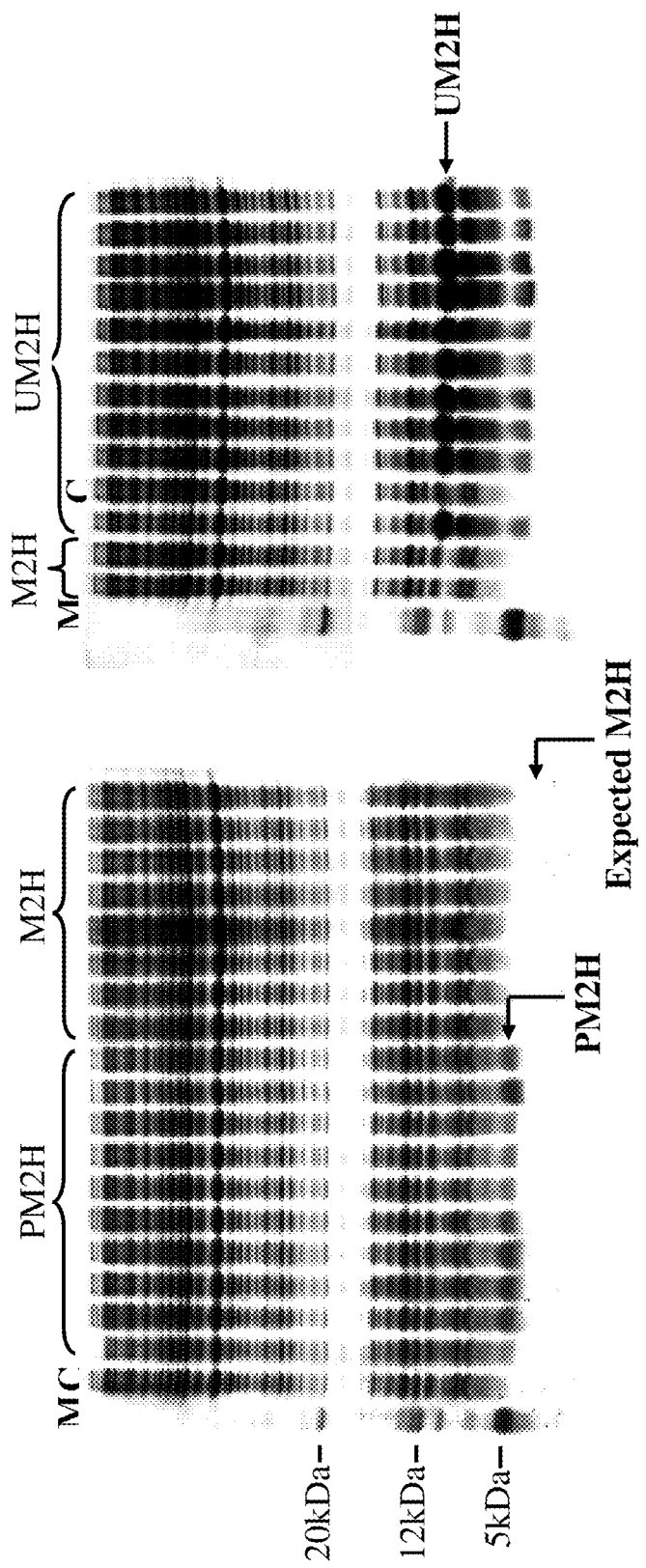
FIG. 2: SDS-PAGE profiles of expressed pET21c-M$_2$H, pET21c-PM$_2$H and pET21c-UM$_2$H in *E. coli* BL21.

For small scale expression transformed cultures were grown overnight at 37° C. in 10 mL of LB medium (10 g Tryptone, 5 g Yeast Extract and 10 g NaCl per liter) containing 100 micromolar of ampicillin to an OD600 of approximately 1.5. Protein expression was induced by addition of 10 microliter of 250 mM solution of IPTG and the bacterial culture was allowed to grow for 4 hours post-induction at 37° C. Cells were harvested by centrifugation and recombinant proteins were detected by SDS-polyacrylamide gel electrophoresis (with 15% resolving gels). To prepare samples, they were boiled in SDS loading buffer with a reducing agent for 5 minutes. Results, pictured in FIG. 2, indicated that while the construct lacking the expression enhancer (SEQ ID NO: 14) did not appear to be expressed to any detectable level, the other constructs with expression enhancers were clearly overexpressed. PM2H (SEQ ID NO: 16) appears to have expressed less than UM2H (SEQ ID NO: 18) but we found that MBP8298 may not stain well with Coomassie Blue 8250 that we used to stain the gels. Ubiquitin and Ubiquitin-containing fusion proteins were, on the other hand, stained intensively with the dye. In FIG. 2, untransformed bacterial controls are shown with "C". Marker lane is shown by "M".

It was not known if the recombinant proteins expressed in the above experiments were in soluble form inside the bacteria or deposited in insoluble inclusion bodies. To address this, cell pellets from the small scale production were suspended in 25 mM Tris-HCl pH 8.0 containing 1 mM EDTA, incubated on ice for at least 10 minutes and subsequently sonicated using a sonicator until all cells were broken as evident by microscopic examination. Samples were then centrifugation at 14,000 g for 10 minutes and both pellets and supernatants were analyzed by SDS-polyacrylamide gel electrophoresis (with 15% resolving gels). Comparing the protein profiles of pellets and supernatants, it was determined that UM$_2$H was expressed in soluble form whereas PM$_2$H was precipitated in inclusion bodies.

3. Production by Fermentation

The PM$_2$H construct, shown above to over-express and deposit the recombinant proteins in inclusion bodies, was used for fermentation production. To prepare the inoculum a bacterial culture containing the PM$_2$H expression vector was inoculated into 100 mL of LB culture medium containing 100 micromolar of ampicillin and grown overnight at 37° C. The inoculum was transferred into a ~1.5-L fermenter containing 1 L of modified TB medium (12 g Tryptone, 24 g Yeast Extract, 4 mL glycerol, 1 g glucose, 3.46 g KH$_2$PO$_4$ and 18.8 g K$_4$HPO$_4$ per liter) and 100 micromolar of ampicillin. The inoculated fermenter was maintained at pH 7.0 and 37° C. with agitation at 500 rpm and 1 L/min air. The culture was induced at OD600 of 20 with the addition of IPTG from a 250 mM solution to the final concentration of 250 micromolar. When nutrients became limiting (as judged by an increase in dissolved oxygen from approximately 30% to near 100%), the culture was fed with additional nutrients (10 g Tryptone, 5 g Yeast Extract, 10 g NaCl and 10 g glucose per liter). The fermentation was stopped 4 hours post-induction and cells were harvested from the culture with centrifugation at 10000 G for 5 minutes. The cell pellet obtained was suspended in 50 mL of 25 mM Tris-HCl pH 8.0 containing 1 mM EDTA, incubated on ice for at least 10 minutes and finally sonicated using a sonicator until all cells were broken and inclusion bodies were released as evident by microscopic examination. Inclusion bodies were pelleted by centrifugation at 14,000 g for 10 minutes and then re-suspended in 50 mL of 25 mM Tris-HCl pH 8.0 containing 1 mM EDTA.

Several conditions were tested for dissolution of the PM$_2$H inclusion bodies. For initial attempts PM$_2$H was dissolved in 50 mM HCl and it was found that heating to 70° C. for 10 minutes could completely dissolve the inclusion bodies. However, higher temperatures appear to disintegrate the peptide as judged by HPLC and mass spectrometric analysis (data not shown). On the other hand, HCl-dissolved PM$_2$H was found to readily precipitate when pH was adjusted to 8.0 using the final concentration of 25 mM Tris-HCl. This pH was significant because the subsequent enzymatic cleavage of the fusion proteins was carried out at pH 8.0. When inclusion bodies were dissolved in 15 mM NaOH and then pH was adjusted to 8.0 no precipitation was immediately detectable. However, over a period of 5-10 hours this changed and precipitation was evident. A number of additives were tested to see if they could stop the slow precipitation of high pH-dissolved PM$_2$H and eventually glycine and glycerol were found to be most useful. Subsequent experiments were, therefore, carried out by dissolving inclusion bodies in 15 mM NaOH for 15 minutes with gentle agitation. Glycine to the final concentration of 100 millimolar and glycerol to the final concentration of 10% were added and pH was decreased to 8.0 over 4 to 5 minutes by gradual addition of Tris-HCl pH 8.0 from a 500 mM solution to the final concentration of 25 mM.

The PM$_2$H solution was heated at 70° C. for 10 minutes to deactivate *E. coli* proteases. No precipitation of PM$_2$H was detected following this treatment as judged by SDS PAGE analysis of the pellet and the supernatant.

Figure 3:
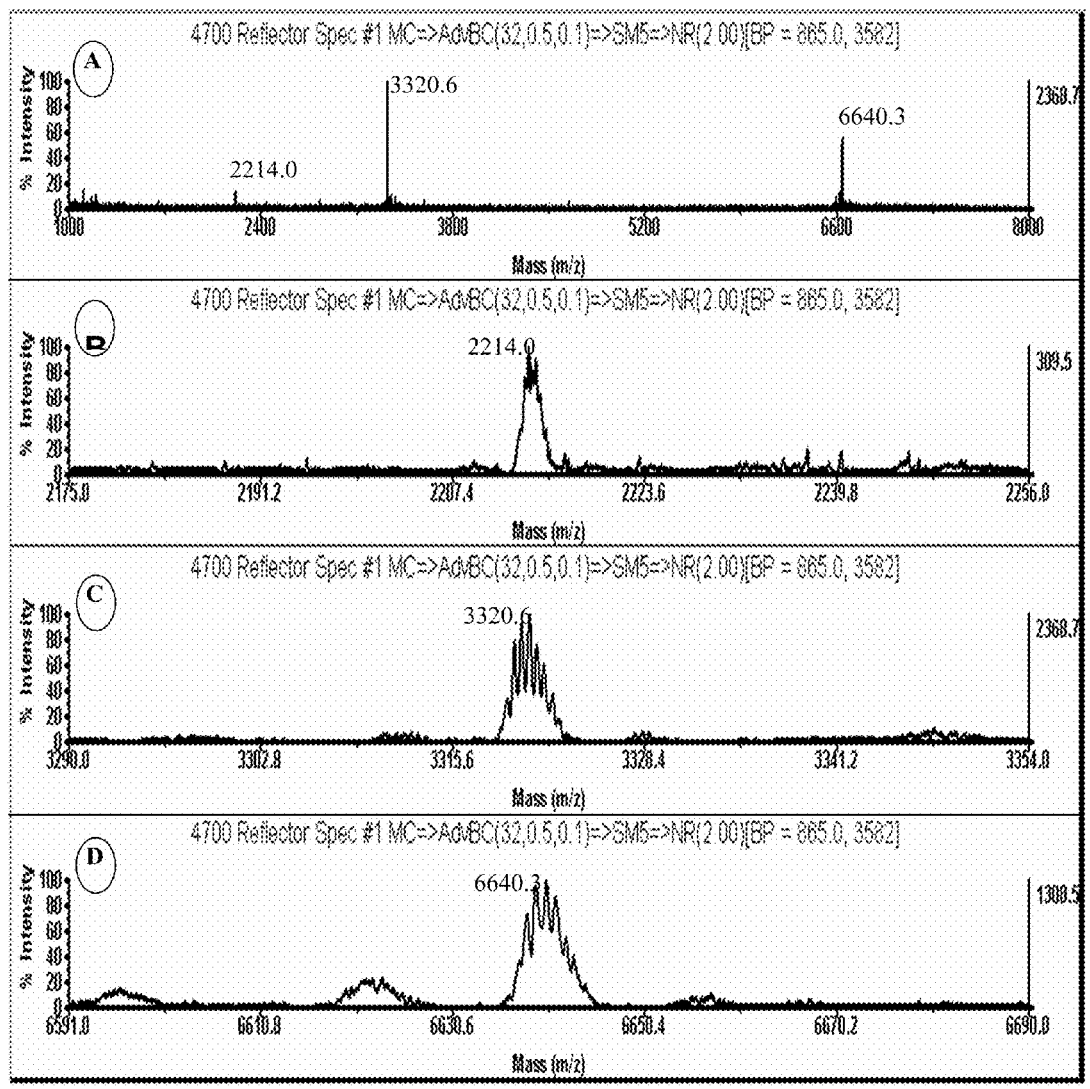
FIG. 3: Mass spectroscopic analysis of PM$_2$H

For mass spectrometric analysis, one microliter of PM$_2$H inclusion bodies were dissolved in 20 microliter of 50 mM HCl. This was diluted 1:10 in 0.1% TFA, 2% acetonitrile and analyzed by a MALDI TOF/TOF mass spectrometer. Results, shown in FIG. 3, indicated the presence of one major species with a mass consistent with that expected for PM2H. The same result was obtained when PM$_2$H was dissolved using the high-pH dissolution method (not shown). In FIG. 3 panel B shows the MALDI spectrum collected from 800 to 8000 m/z. Panel C and D show 3 major ions detected at ~2214.0, 3320.6 and 6640.3 average m/z. The ions were found to be respectively triply, doubly and singly charged forms of one species with estimated average mass of ~6639.2 Da. This is consistent with the expected average mass of PM2H, i.e. 6639.5 Da.

EXAMPLE 5

Figure 4:
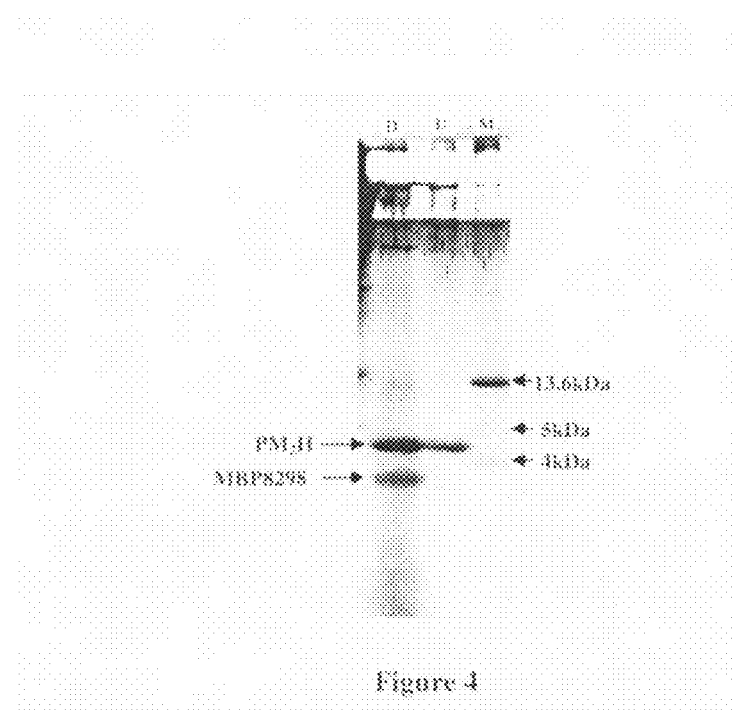
FIG. 4: SDS-PAGE profiles of control and Asp-N digested PM2H.

Enzymatic Cleavage of the Recombinant Protein to Release the MBP8298 Peptide Fifty microliter inclusion bodies (containing approximately 50 µg PM$_2$H protein) was centrifuged and supernatant removed. The pellet was dissolved in 150 microliter of 15 mM NaOH as described in Example 4. Once the solution was adjusted to pH 8.0, twenty microliter of acetonitrile and 1 microliter of 1 mg/mL solution of endoproteinase Asp-N was added and gently mixed. The digestion reaction was allowed to proceed for 16 hours at 37° C. and then stopped by acidification by TFA. FIG. 4 present the result of digestion analyzed by tricine-SDS gel electrophoresis. In the picture lane D contains Asp-N digested PM2H, lane U contains control PM2H and lane M has the marker.

Figure 5:
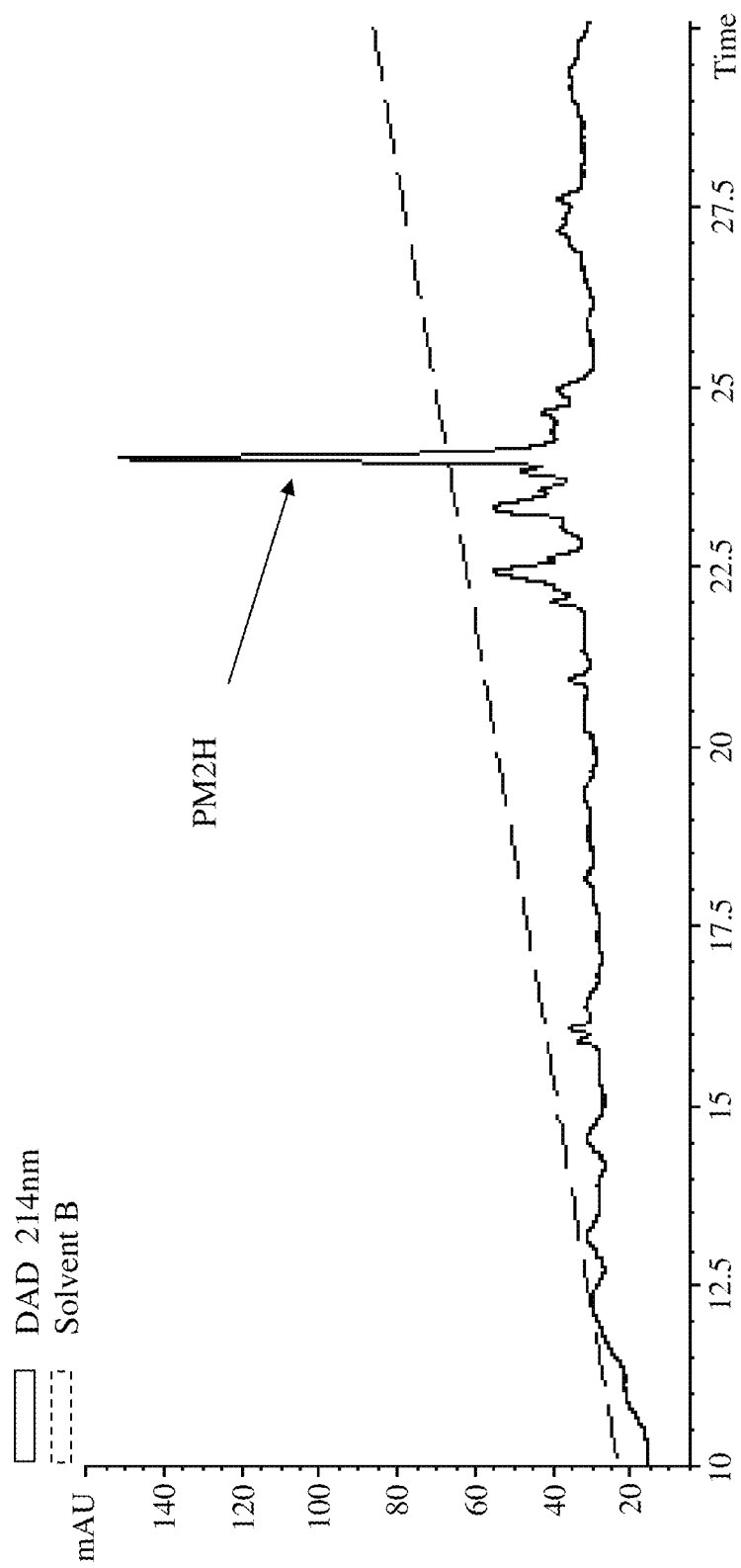
FIG. 5: RP-HPLC profiles of un-digested PM2H.
Figure 6:
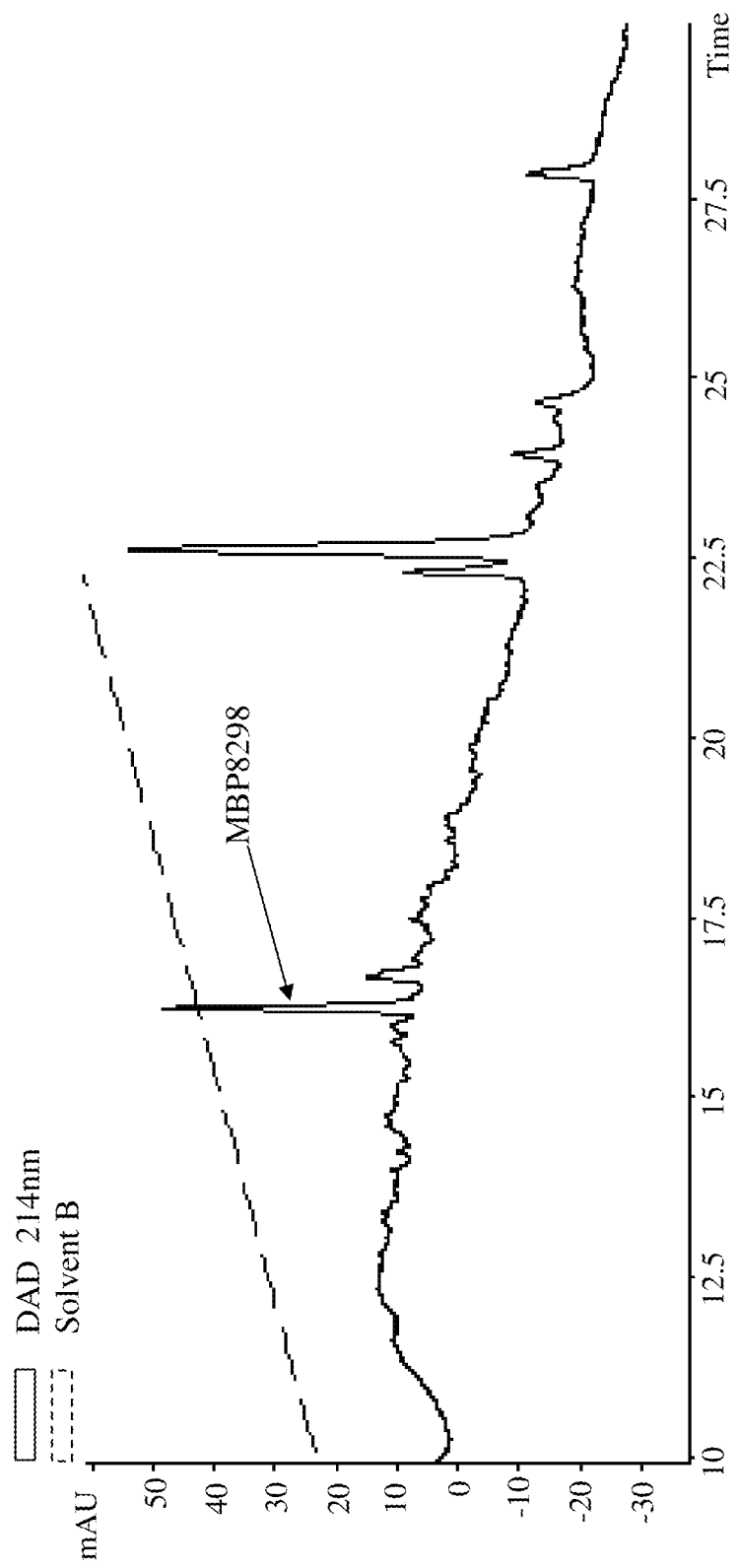
FIG. 6: RP-HPLC profiles of Asp-N digested PM2H.

Samples were also analyzed by HPLC, using a C18 reverse phase column. Solvent A was water containing 0.1% TFA and solvent B was 80% acetonitrile containing 0.1% TFA. The column was run at 40° C. with a 5-100% B gradient over 30 minutes, at a flow rate of 0.6 mL/minute with peptide detection at 214, 260 and 280 nm. In addition, spectrums were recorded by an on-line diode array spectrometer when peaks (at 214 nm) were detected. Under these conditions PM$_2$H was found to elute at 24 minutes equivalent to approximately 42% acetonitrile (in comparison UM$_2$H was eluted at 23.4 minutes equivalent to approximately 40.5% acetonitrile). MBP8298 was eluted at 16.2 minutes equivalent to approximately 22% acetonitrile. FIG. 5 presents a reverse-phase HPLC chromatogram of un-digested PM2H. FIG. 6 displays the Asp-N digested PM2H. Peaks containing PM2H and release MB8298 are respectively shown in the pictures.

Figure 7:
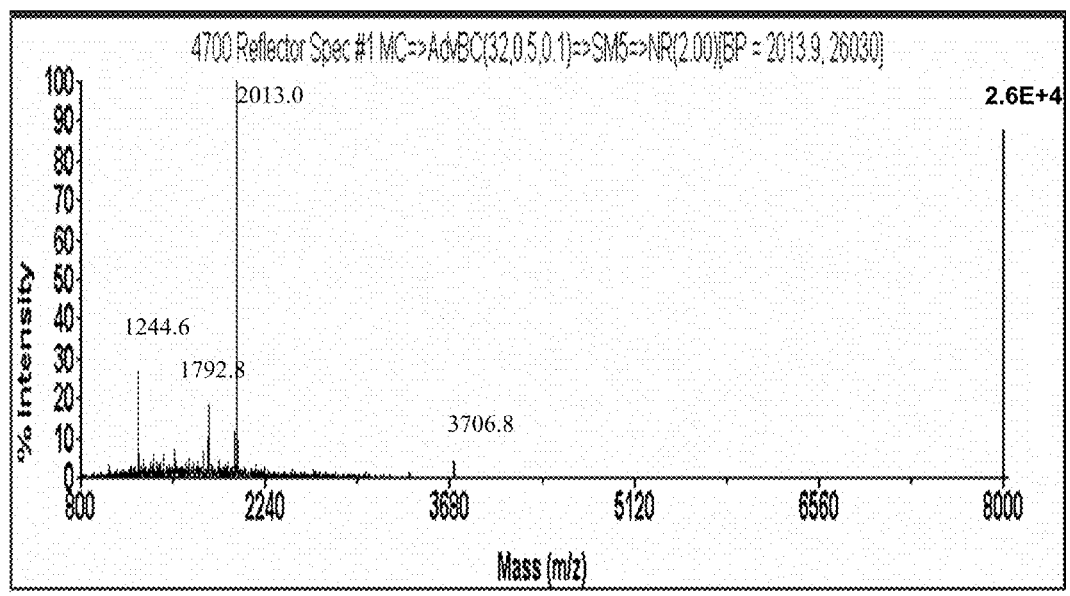
FIG. 7: MS analysis of recombinant MBP8298.
Figure 8:
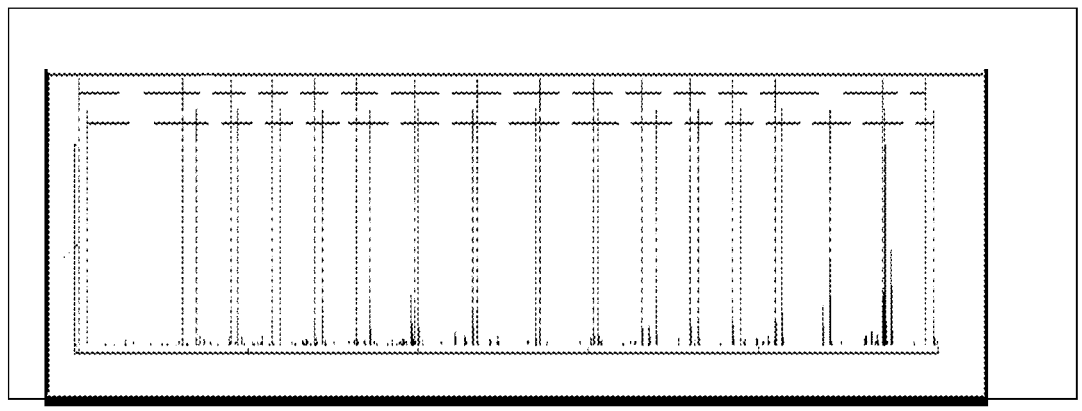
FIG. 8: De novo sequencing analysis of recombinant MBP8298.

For MS analysis the peak eluted at 16.2 minutes in the above HPLC experiment was collected and analyzed by a MALDI TOF/TOF mass spectrometer. Result of the MS analysis, shown in FIG. 7, indicated the presence of one major species with monoisotopic m/z of 2013.0 (i.e. mass of 2012.0 Da). This is consistent with that expected mass for MBP8298 (that is 2012.05 Da). De novo sequencing analysis of this species, shown in FIG. 8, resulted in a sequence consistent with that of MBP8298, i.e. DENPVVHFFKNIVTPRT (SEQ ID NO: 1).

The description of the embodiment set forth above is intended to be illustrative rather than exhaustive of the present invention. It should be appreciated that those of ordinary skill in the art may make certain modifications, additions or changes to the described embodiment without departing from the spirit and scope of this invention as claimed hereinafter.

What is claimed is:

1. A method for predicting the expression efficiency for recombinant production of a protein by prokaryotic cells, the method comprising the steps of:
   a) providing a mRNA sequence which codes for the protein to be produced, wherein said mRNA includes a translation initiation region (TIR);
   b) predicting a secondary structures for a 5' region of said mRNA by a computer program executed on a computer;
   c) estimating the probability of said mRNA structure;
   d) calculating the fraction of unfolded TIR for said mRNA structure according to:

$$F_u = \frac{1}{\exp\left(\frac{-\delta G_{TIR}}{Tk}\right) + 1}$$

in which Fu is fraction of unfolded TIR, δGTIR is free energy of TIR (kcal/mole), T is the absolute temperature and k is the Boltzmann constant (0.001986266 kcal/mole/degree K);
   e) calculating probability of unfolded TIR in said mRNA sequence based on:

$$P_u = P_S \times F_u$$

in which $P_u$ is probability of unfolded TIR, $P_S$ is said probability of mRNA structure (of step c) and Fu is said fraction of unfolded TIR for said structure of step d; and
   linking said probability of unfolded TIR (of step e) with predetermined expression Efficiencies.

2. The method of claim 1, wherein the prediction is improved by using an averaged estimate based on at least 2 different lengths of the 5' region of mRNA.

3. The method of claim 1, wherein a number of most likely secondary structure (that is one optimal and a number of sub-optimal structures) for said mRNA are used.

4. The method of claim 3, wherein the likely secondary structures within a minimum of approximately 5% from the global minimum free energy of said mRNA (5% sub-optimality) are used.

5. The method of claim 4, wherein the likely secondary structures within a minimum of approximately 10% from the global minimum free energy of said mRNA (10% sub-optimality) are used.

6. The method of claim 1, wherein the translation initiation region on said mRNA includes the sequences starting from approximately nucleotide −15 and ending with approximately nucleotide +16, (with the A of the AUG start codon as +1 and the one before it as −1).

7. The method of claim 1, wherein expression efficiency is estimated by the formula:

$$E = \frac{Pu}{Pu + A}$$

in which E is expression measured as the fraction of the maximum expressible of said protein and $P_u$ is said probability of infolded TIR, A is a system-dependent variable (approximately 0.009) that depend on the cell and the proteome being expressed.

* * * * *